(12) United States Patent
Prestidge et al.

(10) Patent No.: US 7,014,623 B2
(45) Date of Patent: Mar. 21, 2006

(54) BODY HEAT ACTUATED PARENTERAL DEVICE

(76) Inventors: Dean Brian Prestidge, 7 Key West Drive, Mullaloo, Western Australia 6027 (AU); Maxwell Edmund Whisson, 5/70 Subiaco Road, Subiaco, Western Australia 6008 (AU)

( * ) Notice: Subject to any disclaimer, the term of this patent is extended or adjusted under 35 U.S.C. 154(b) by 206 days.

(21) Appl. No.: 10/483,517

(22) PCT Filed: Oct. 5, 2001

(86) PCT No.: PCT/AU01/01253

§ 371 (c)(1),
(2), (4) Date: Jan. 9, 2004

(87) PCT Pub. No.: WO02/28458

PCT Pub. Date: Apr. 11, 2002

(65) Prior Publication Data

US 2004/0193109 A1    Sep. 30, 2004

(30) Foreign Application Priority Data

Oct. 6, 2000 (AU) ..................... PR0568
Apr. 9, 2001 (AU) ..................... PR4286
Apr. 17, 2001 (AU) ..................... PR4412

(51) Int. Cl.
*A61M 5/00* (2006.01)
*A61M 5/32* (2006.01)

(52) U.S. Cl. ..................... 604/110; 604/192
(58) Field of Classification Search ............. None
See application file for complete search history.

(56) References Cited

U.S. PATENT DOCUMENTS

| 5,104,384 | A |   | 4/1992 | Parry |
| 5,176,655 | A | * | 1/1993 | McCormick et al. ....... 604/198 |
| 5,431,630 | A | * | 7/1995 | Leonard .................... 604/110 |
| 5,501,672 | A | * | 3/1996 | Firth et al. ................. 604/177 |
| 5,795,336 | A |   | 8/1998 | Romano et al. |

FOREIGN PATENT DOCUMENTS

| GB | 2 327 614 | 2/1999 |
| WO | 00/40281 | 7/2000 |
| WO | 00/40287 | 7/2000 |

* cited by examiner

*Primary Examiner*—Michael J. Hayes
(74) *Attorney, Agent, or Firm*—Bachman & LaPointe, P.C.

(57) ABSTRACT

A needle apparatus (10) includes a tubular needle (20) with a sharp point (22). The apparatus also includes a shielding means and movement means (17) in which the movement means is temperature sensitive. Upon the needle being inserted into tissue the movement means is heated by body heat and causes the needle and the shielding means to move relatively to render the sharp point safe. Preferably the movement means contains shape memory alloy.

16 Claims, 14 Drawing Sheets

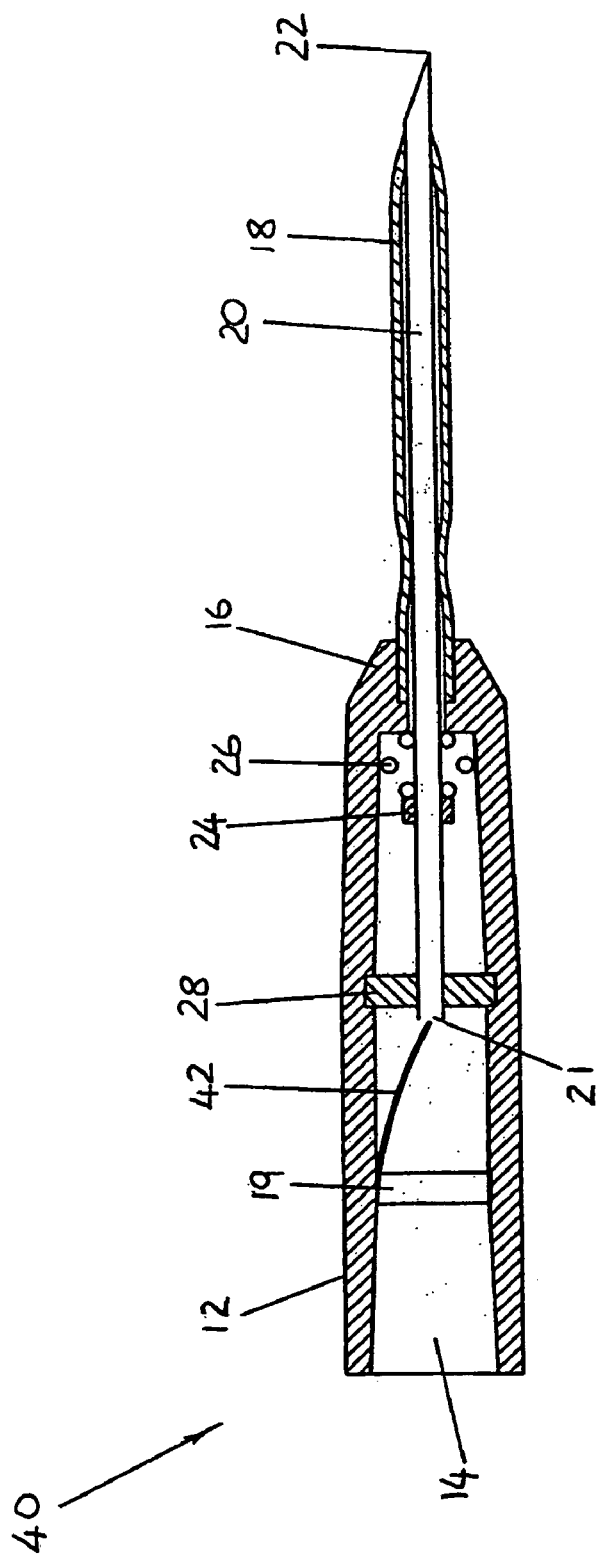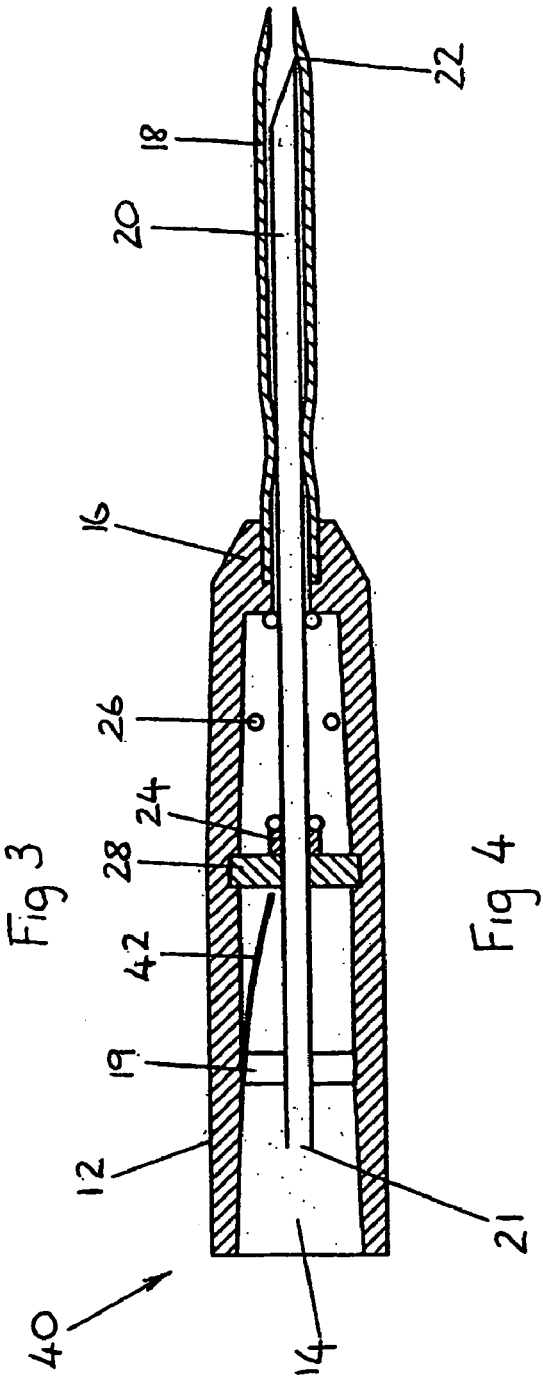

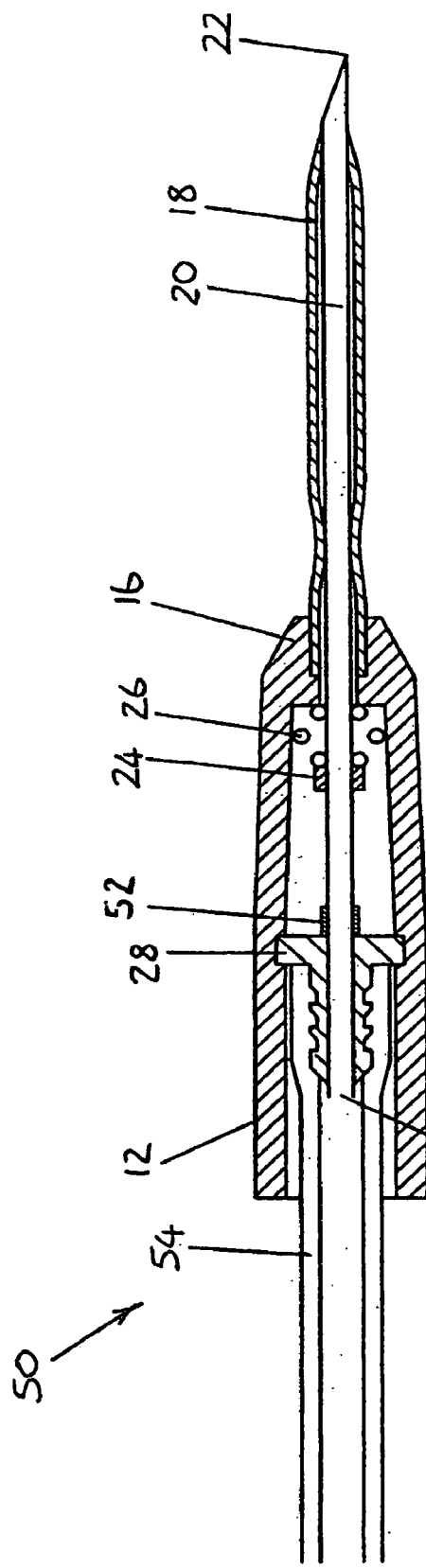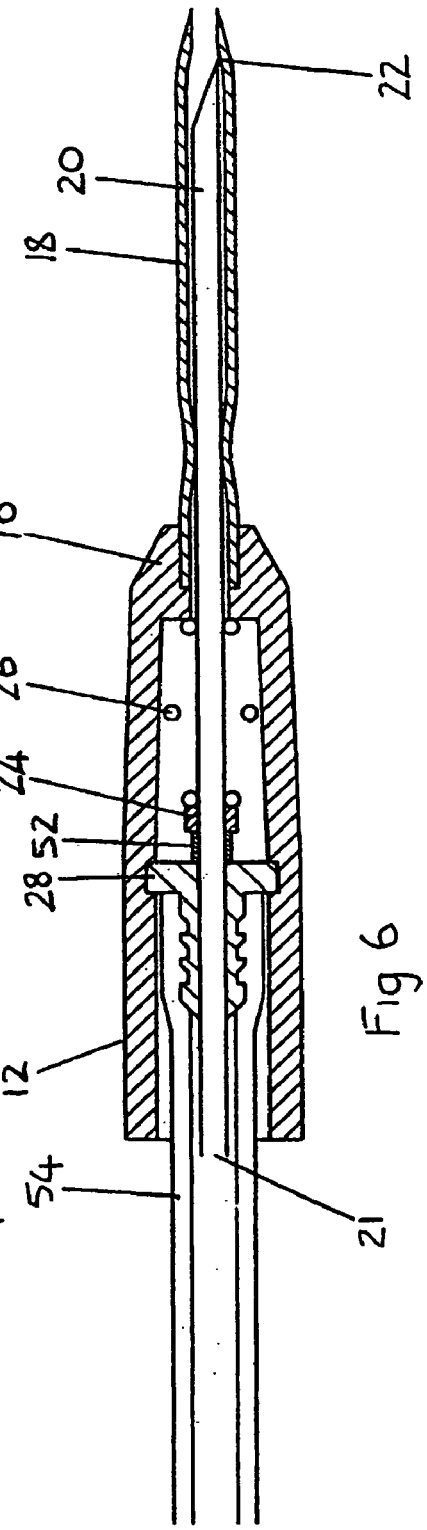

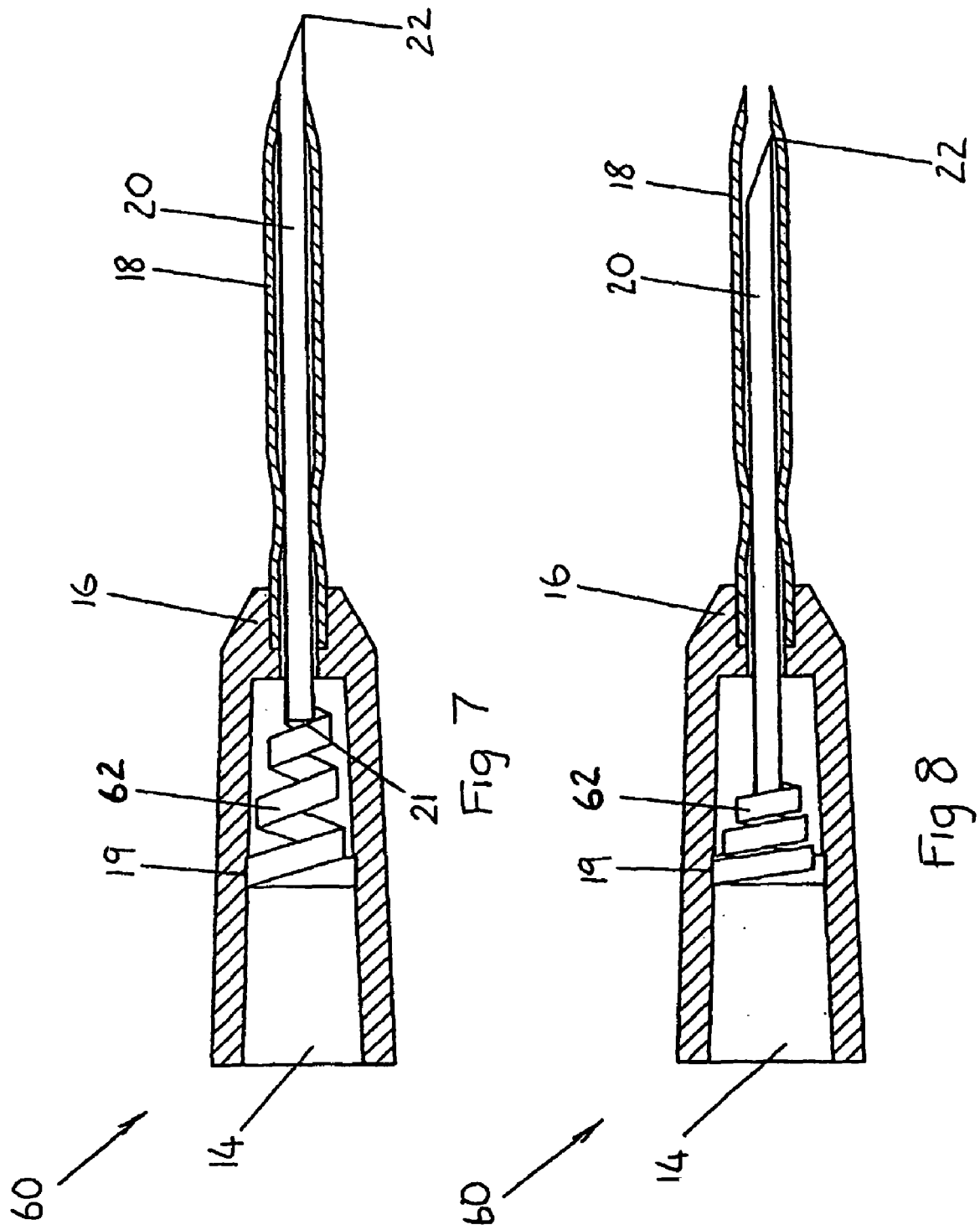

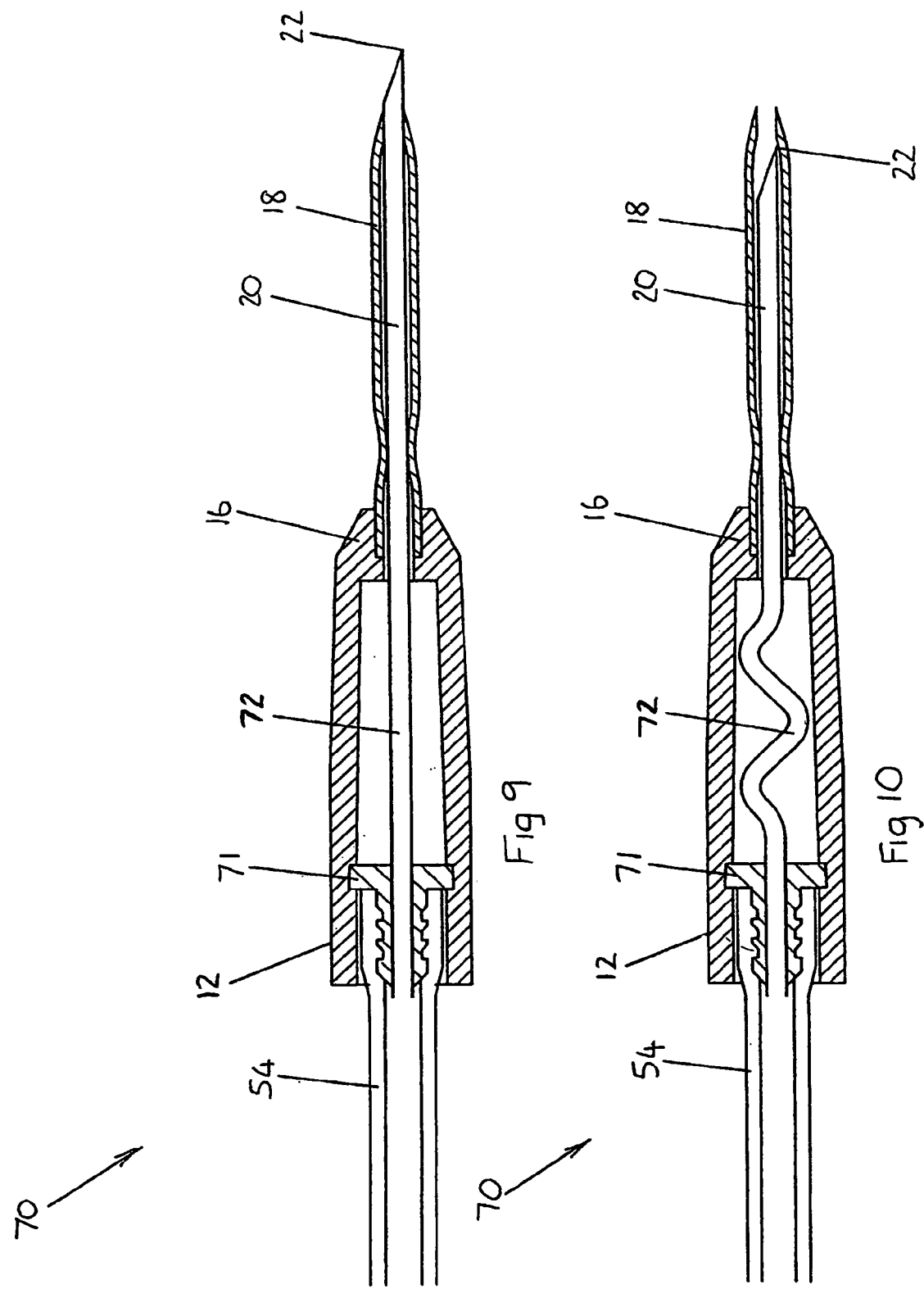

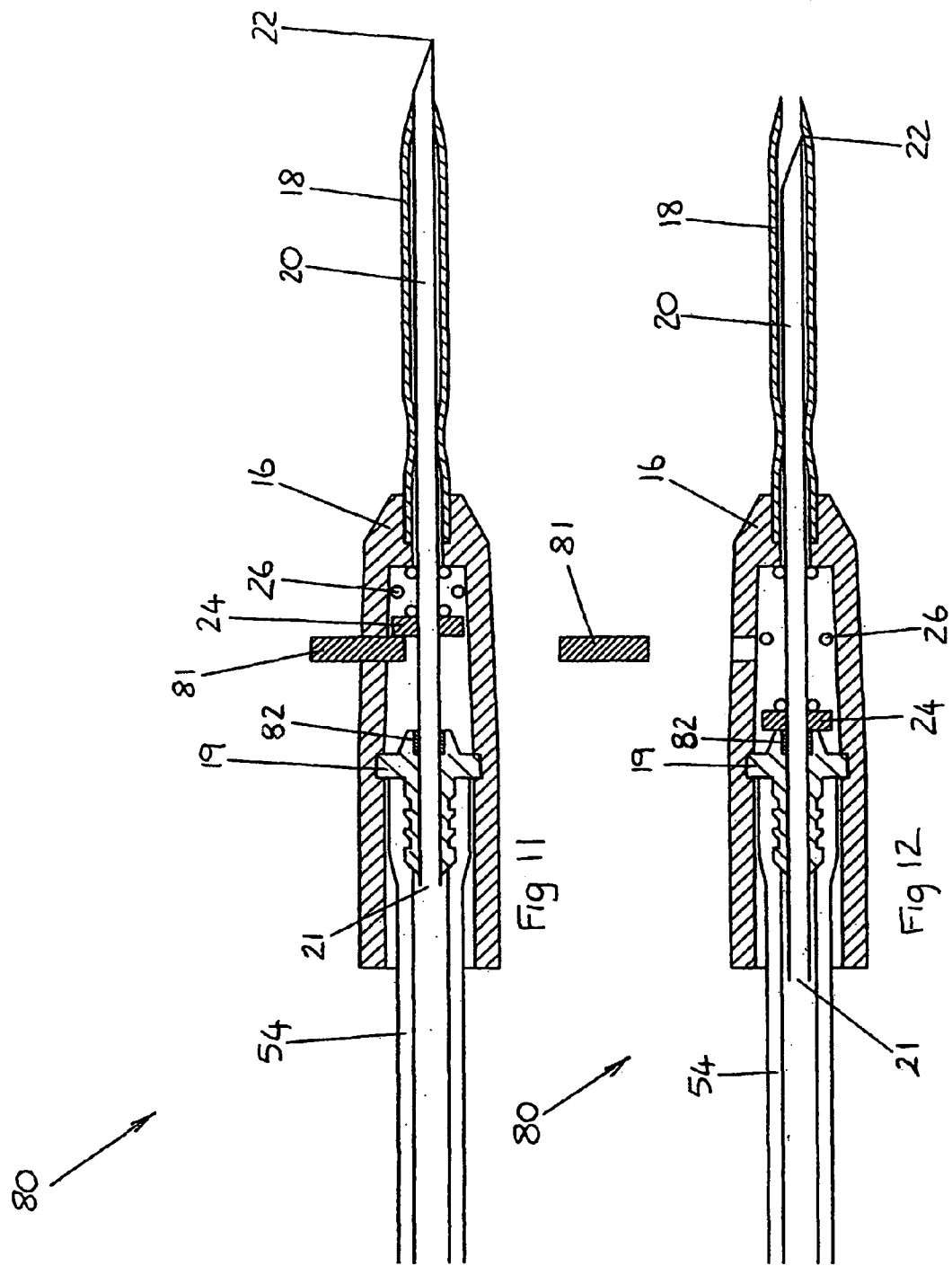

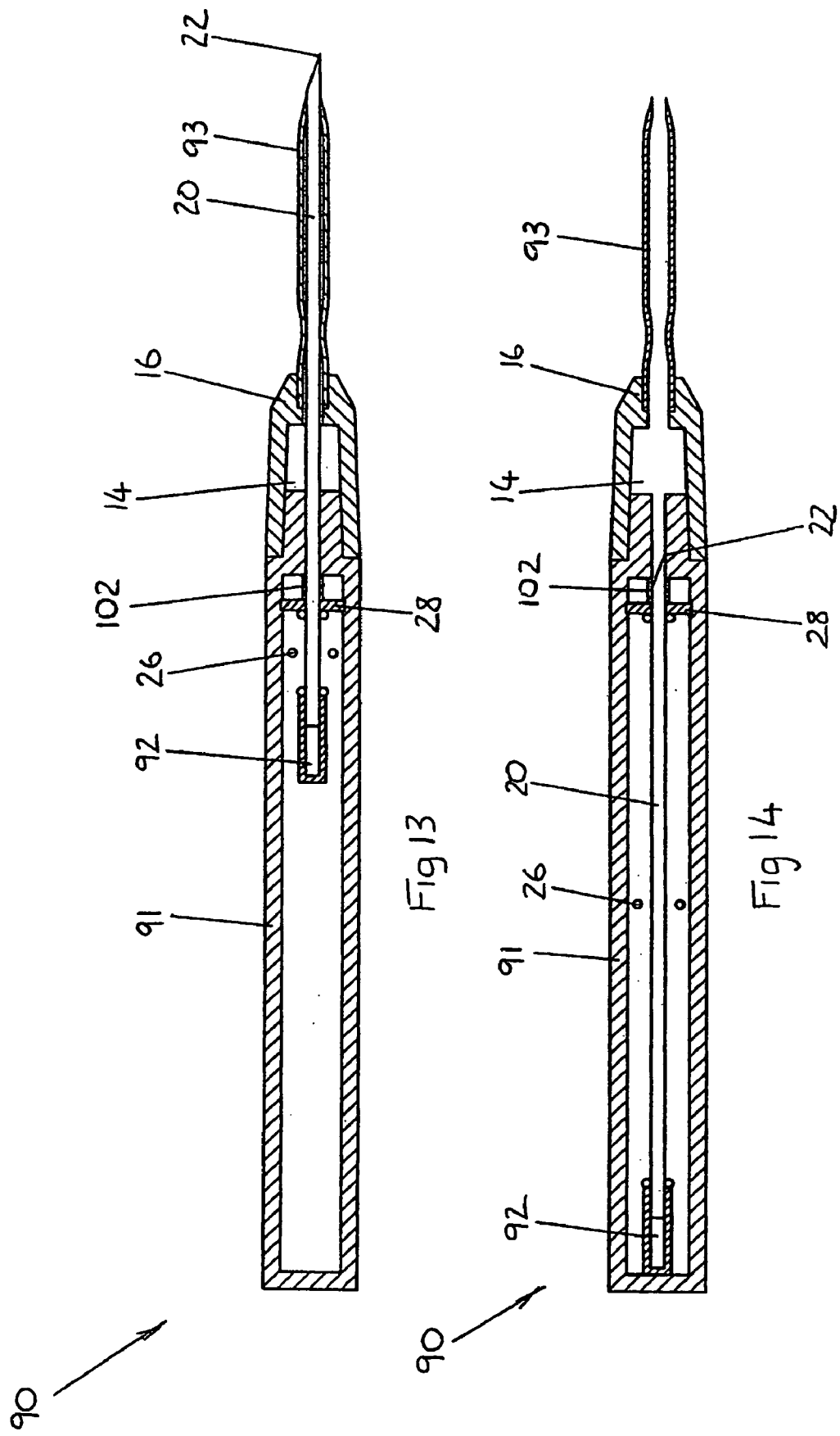

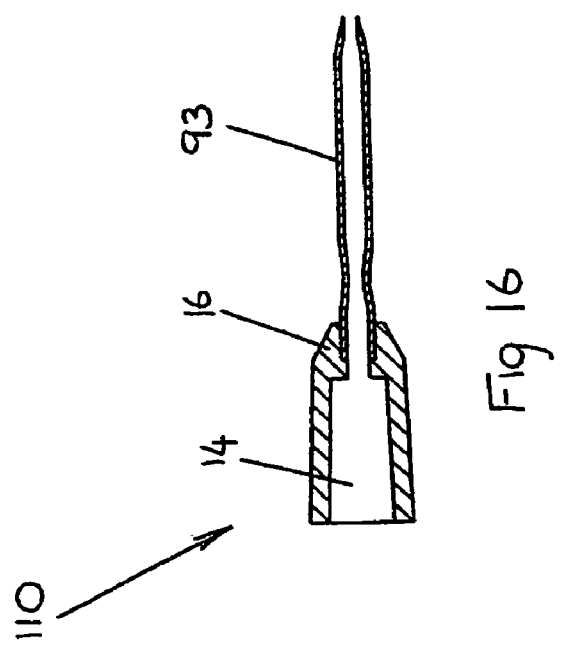
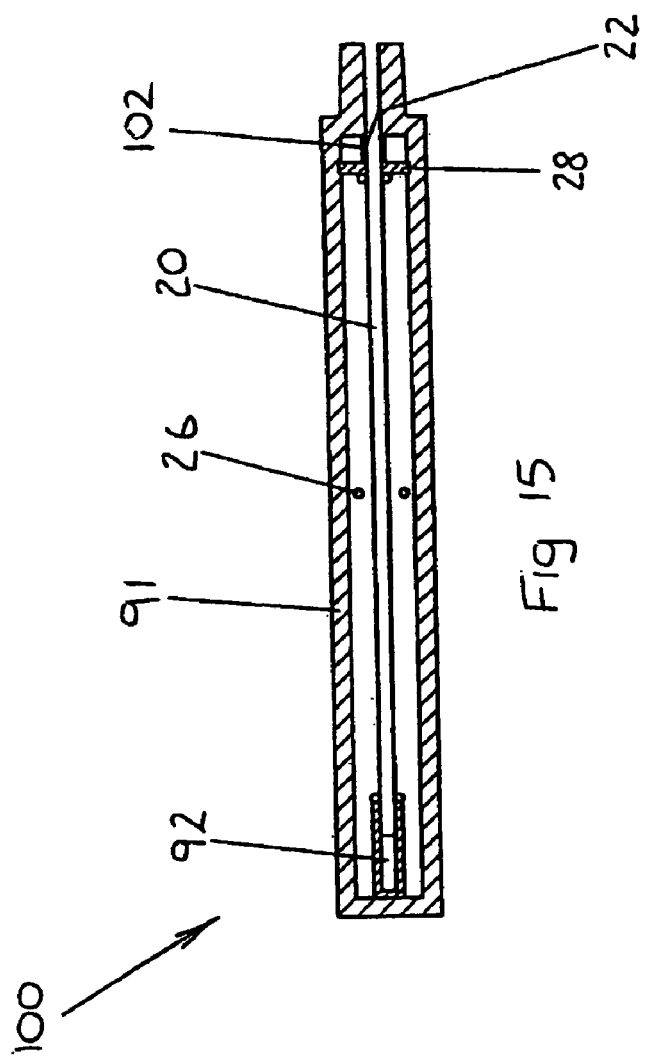

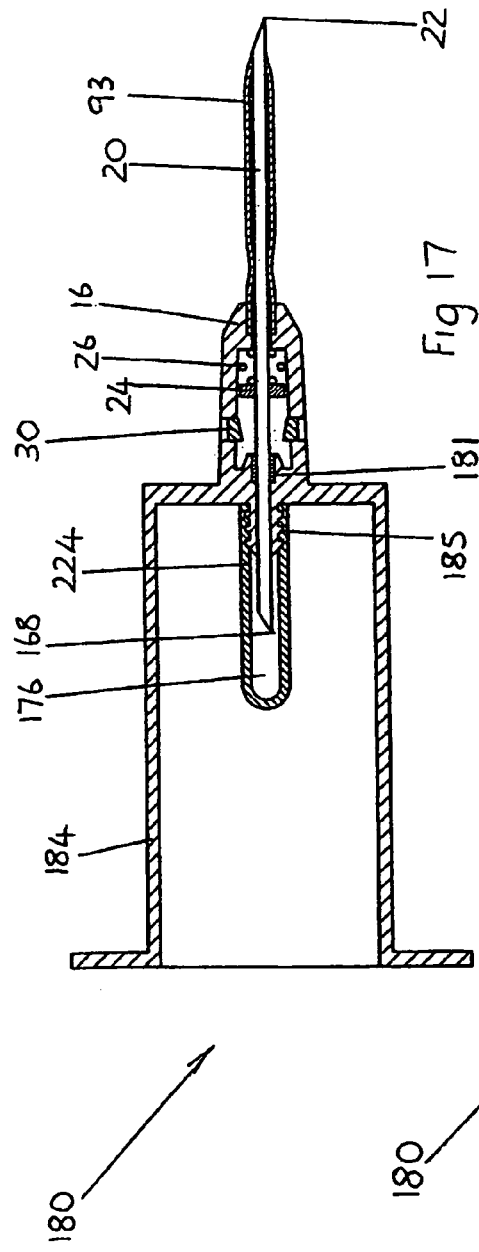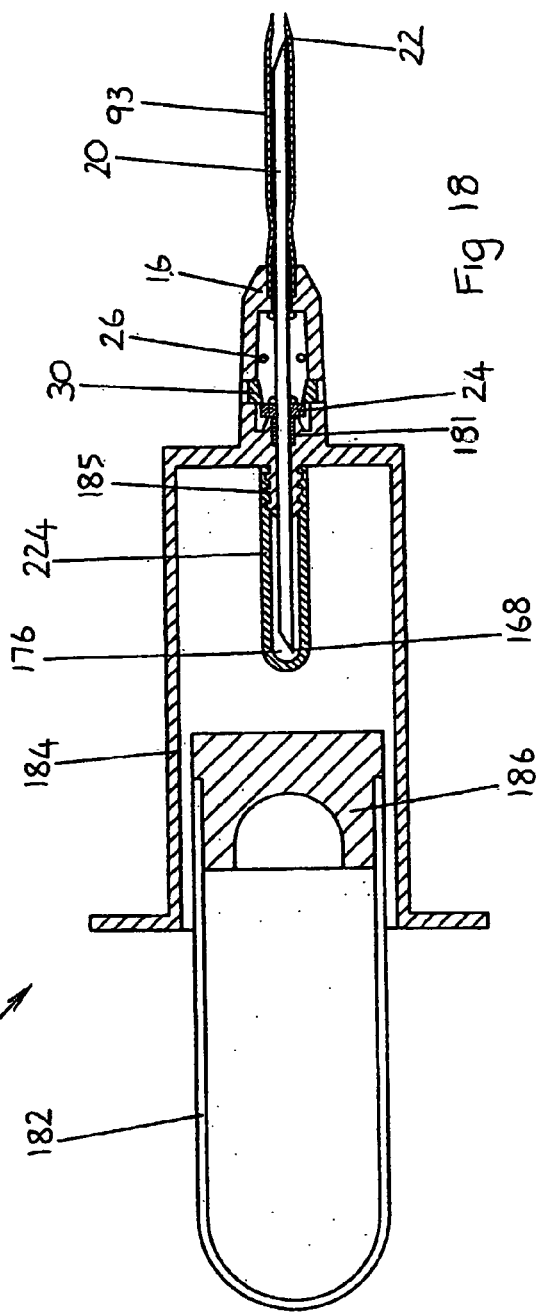

BODY HEAT ACTUATED PARENTERAL DEVICE

FIELD OF THE INVENTION

The present invention relates to a heat sensitive needle apparatus.

PRIOR ART

Injection devices which use a sharp needle to enter human tissue are now widely recognized as being hazardous to users and other individuals because the sharp point, contaminated by its exposure to the tissue of the first person may penetrate the skin of a second person and in doing so may carry micro-organisms from the patient on whom the injection device was first used into the tissue of a second person. Such transmission may result in the development of disease in the second person and when the puncture of the skin is accidental it is referred to as "needlestick injury" or "needle-prick injury".

A sharp pointed needle may also cause injury to the patient during a parenteral procedure. For example, if the patient moves unexpectedly or the device is inappropriately moved by the operator the sharp point may move to an undesirable location. If the point is in a vein in preparation for an intravenous injection or for the sampling of blood for pathology testing, the needle point may easily pierce the wall of the vein. If medication is being infused it will then pass into the tissue around the vein. If blood is being sampled the flow will stop and a bruise may develop due to flow of blood through the vein wall into the tissue. To avoid these complications a soft flexible tube called a catheter may be preferred for establishing fluid connection between the tissue or the bloodstream and apparatus outside the body.

In other arrangements designed to prevent unwanted damage or disease transmission by the needle point, a blunt sheath, a catheter, or an internal rod or tube may move axially with respect to the needle so as to extend beyond the sharp needle point, so preventing it from puncturing tissue inappropriately or dangerously. Such arrangements however generally suffer from the disadvantage that the operator is required to move a latch, releasing a spring to perform the required axial movement or alternatively the operator is required to move the part of the injection apparatus or the protecting catheter, rod, cap or tube in such a way as to prevent the needle point from being hazardous. Several such arrangements have been proposed and some are in commercial development or are available commercially. All suffer from dependence of the safety mechanism on deliberate action by the operator in various degrees. Also, the action of releasing or actuating the safety mechanism may interfere with or act as a distraction from efficient performance of the operation for which the injection apparatus is being used.

In addition, such mechanisms require the provision of a handle means such as a sliding tab or a button to be depressed by a finger tip or an area to be squeezed or a rod, a tube or a filament to be withdrawn from the device during or after completion of these procedures. Such mechanisms tend to compromise clinically and commercially optimal design and construction.

BRIEF DESCRIPTION OF THE INVENTION

It is an object of the present invention to provide a needle apparatus in which problems of the prior art are at least alleviated.

In accordance with one aspect of the present invention there is provided a needle apparatus comprising a tubular needle having a sharp point characterised in that there is provided a shielding means and a movement means for moving the needle and the shielding means relative to one another from an operative position in which the sharp point of the needle is exposed to an inoperative position in which the sharp point of the needle is shielded by the shielding means so as to reduce the possibility of tissue being punctured by the needle, wherein the movement means comprises a component which is responsive to body heat such that when the needle is inserted into tissue, in use, the movement means is exposed to body temperature and the resulting change in temperature of the movement means causes the needle and the shielding means to be moved relatively automatically to the inoperative position.

BRIEF DESCRIPTION OF THE DRAWINGS

The present invention will now be described, by way of example, with reference to the accompanying drawings, in which:

FIG. 3 is a cross-sectional view of a second embodiment of a needle apparatus in accordance with the present invention showing the apparatus with a needle point as supplied extended beyond an enclosing sleeve or cannula, ready to pierce tissue;

FIG. 4 is a view similar to FIG. 3 in which a latch has moved to release the needle assembly allowing it to move to a position in which the needle point is located within the cannula;

FIG. 5 is a cross-sectional view of a third embodiment of a needle apparatus in accordance with the present invention showing the apparatus with a needle point as supplied, extended beyond an enclosing sleeve, ready to pierce tissue;

FIG. 6 is a view similar to FIG. 5 in which a latch has released a needle assembly allowing the needle assembly to move to a position in which the needle point is located within the sleeve;

FIG. 7 is a cross-sectional view of a fourth embodiment of a needle apparatus in accordance with the present invention showing the apparatus with a needle point as supplied, extended beyond an enclosing sleeve, ready to pierce tissue;

FIG. 8 is a view similar to FIG. 7 in which the needle assembly has been moved to a position in which the point of the needle is located within the sleeve;

FIG. 9 is a cross-sectional view of a fifth embodiment of a needle apparatus in accordance with the present invention showing the apparatus with a needle point as supplied, in a first position extended beyond an enclosing sleeve, ready to pierce tissue;

FIG. 10 is a view similar to FIG. 9 in which the needle assembly has been moved so moving the needle point to a second position located within the sleeve;

FIG. 11 is a cross-sectional view of a sixth embodiment of a needle apparatus in accordance with the present invention showing the apparatus with a needle point as supplied, extended beyond an enclosing sleeve, in a first position, ready to pierce tissue but restrained from moving into the sleeve by a manually operable stop;

FIG. 12 is a view similar to FIG. 11 in which the manually operable stop has been released, the needle assembly has been used and the needle assembly has been allowed to move to a position in which the needle point is located within the sleeve;

FIG. 13 is a cross-sectional view of a seventh embodiment of a needle apparatus in accordance with the present invention suitable for use in introducing a flexible catheter into a living body, showing the apparatus with a needle point as supplied, extended beyond an enclosing catheter;

FIG. 14 is a view similar to FIG. 13 in which the needle assembly has been allowed to move to a position in which it is enclosed within a needle housing;

FIG. 15 is a view similar to FIG. 14 in which the needle housing, after the needle has been allowed to move, is removed from a Luer fitting, shown in FIG. 16, ready for disposal;

FIG. 17 is a cross-sectional view of an eighth embodiment of a needle apparatus in accordance with the present invention suitable for sampling blood into vacuum tubes and shown ready for insertion into a vein;

FIG. 18 is a view similar to FIG. 17 in which the needle assembly has been allowed to move to a position in which a needle point is enclosed within a close-fitting sleeve and a vacuum sampling tube is shown ready to be advanced within a housing of the needle apparatus;

DESCRIPTION

The needle apparatus of the present invention will now be described in greater detail by reference to the accompanying drawings, in which the same reference numbers are used to refer to similar parts throughout.

Figure 1:
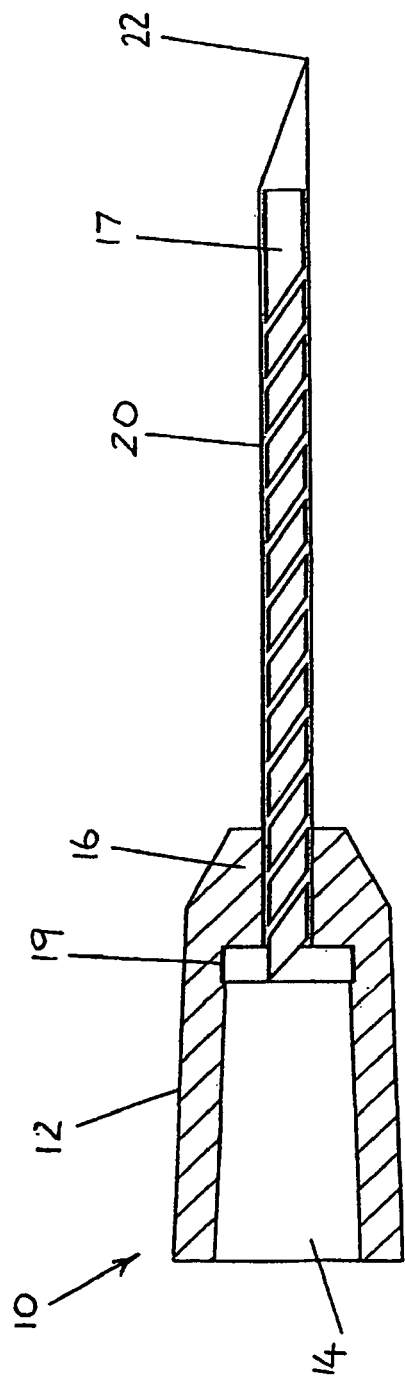
FIG. 1 is a cross-sectional view of a first embodiment of a needle apparatus in accordance with the present invention showing the apparatus with a needle point as supplied and ready to pierce tissue.
Figure 2:
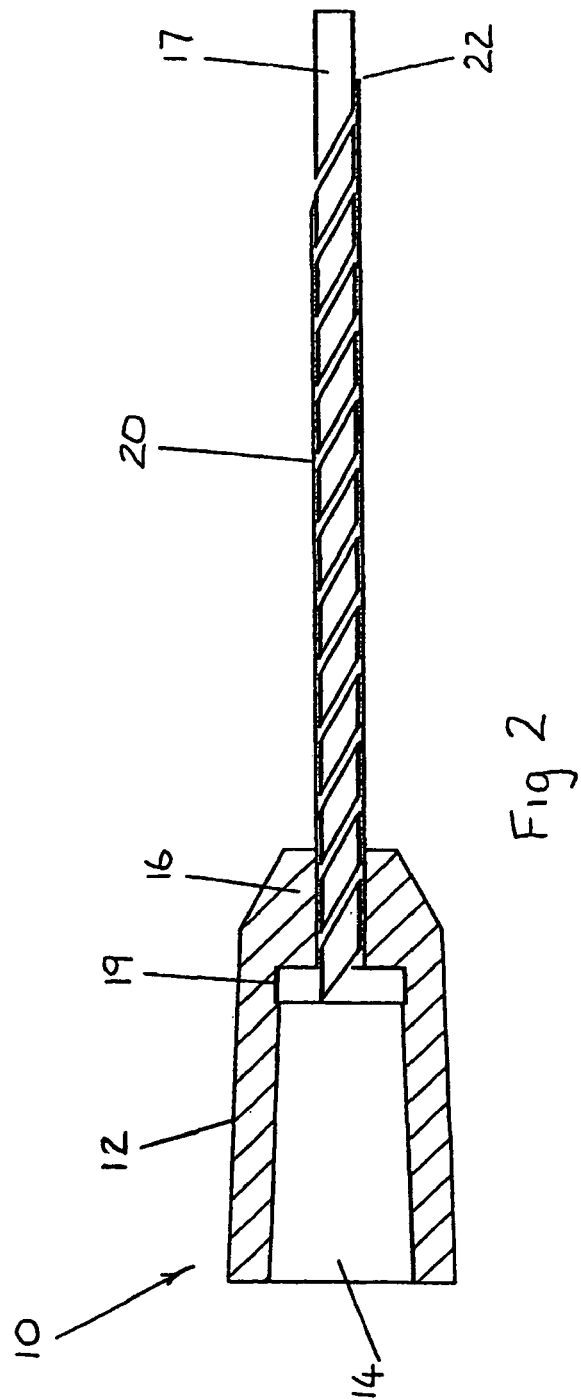
FIG. 2 is a view similar to FIG. 1 in which an insert is extended beyond a needle point so rendering the needle safe.

In FIGS. 1 and 2 of the accompanying drawings there is shown a needle apparatus 10 in accordance with the present invention. In FIG. 1 the needle apparatus 10 is in a first position ready for use to pierce body tissue and transfer fluid to or from the tissue and in FIG. 2 the needle apparatus is shown in a second position after having pierced body tissue and having been warmed by it.

The needle apparatus 10 comprises a Luer or similar housing 12 having an open end 14 and a closed end 16. A metal needle 20 is mounted in the end 16 of the housing 12 and extends away from the end 16. The needle 20 has a sharp point 22. A thin flat coil 17 of heat sensitive metal alloy is formed from a ribbon of the alloy, and has an enlarged partition 19 located within the housing 12. There is thus a fluid flow path through the needle 20 into the housing 12. The coil 17 is formed of a heat sensitive metal alloy which, when heated to near body temperature, automatically causes the coil 17 to lengthen to the position shown in FIG. 2. In this position the coil 17 projects beyond the sharp point 22 and thus renders the needle 20 safe by shielding or obscuring the needle 20 and therefore prevents the sharp point 22 from piercing tissue.

Conveniently, the coil 17 may be formed of a shape memory alloy or SMA. Shape Memory Alloys (SMAs) are already used extensively in such medical devices as stents for dilating arteries or other channels within the human body. Such devices achieve the desired final shape automatically as a result of the transfer of heat into the device as a consequence of being placed within the human body in which the temperature is generally at least 10 degrees centigrade above the ambient temperature of a procedure room in a clinic or operating theatre. It is indeed an essential feature of such devices that they do not reach the temperature required to produce a heat-induced shape until they are within the human body.

Shape Memory Alloys (SMA) usually consist of nickel and titanium (NiTi), but may contain other metals to confer desired properties on the alloy. NiTi SMA can exist in three different phases: a soft martensite at low temperatures, a stronger and more rigid parent-phase austenite at higher temperatures and a superelastic phase, formed when the warm austenite is subjected to stress which reverts to the austenite form when the stress is removed. The temperature at which martensite begins to change to austenite is called the "austenite start temperature:, or simply "start temperature". The temperature at which transformation to austenite is complete is called the "austenite finish temperature". Cooling restores the martensite phase but the temperature at which this begins is much lower than the austenite start temperature due to hysteresis. Typically, a NiTi SMA designed to transform to austenite at body temperature must be cooled to less than 5 deg C. before it begins to return to the softer martensite phase. The NiTi response to a change in temperature can result in a change in shape which is programmable. A selected shape may be formed in the austenite phase at high temperature. Another shape may be cold formed in the martensite phase. When the cool SMA is heated to the selected start temperature the preformed austenite shape begins to return and is completely restored at the finish temperature. The strong high tensile austenite phase is also restored and at usual ambient temperatures is retained due to the hysteresis of the alloy. Two shapes may also be programmed to appear at selected temperatures by a more complex process of repeated temperature cycling. The toughness and tensile strength of the autstenite form of NiTi is comparable to that of stainless steel and its biocompatibility is superior to stainless steel, titanium and titanium-aluminium alloys.

Shape Memory Alloys are discussed in detail in the publication by Jorma Ryhanen in Acta Universitatis Ouluensis "Biocompatibility Evaluation of Nickel-Titanium Shape Memory Metal Alloy", Department of Surgery, University of Oulu, Oulu, Finland, ISBN 951-42-5221-7 and ISBN 951-42-5206-3

It has now been discovered that the properties of SMAs can be used to advantage in needle apparatuses. An essential feature of needle apparatuses such as hypodermic needles, syringes, vacuum operated blood sampling devices, blood donation collecting needles and intravenous infusion lines is that all of the device apart from the needle or catheter within the desired location in the tissue is outside the living body. For a body heat actuated system to alter automatically the conformation of a needle device it is therefore necessary for body heat to be conducted outward to a heat sensitive member. In fact, in most parenteral procedures, blood is first withdrawn from a blood vessel in a test known as "flashback". The sight of blood coming from the back of a catheter or needle confirms that the device is properly located in a vein. Heat conveyed by the blood can also provide this information and U.S. Pat. No. 5,743,882 describes the use of thermochromic liquid crystals to reveal an increase in temperature for just this purpose. Even without a flow of blood however, heat is conducted out of the body through a metal needle, causing a rise in temperature not only of the part of the needle within the tissue but also of the part of the needle outside the body, the more so if the outside part is surrounded by a heat insulator. SMAs are now available which can be formed in such a way as to change their properties and shape dramatically at selected temperatures. SMAs usually comprise a mixture of nickel and titanium and the temperature at which the shape changes, called the transformation temperature can be adjusted by careful choice of the ratio of nickel to titanium. The temperature at which transformation leading to the shape change begins to occur is called the start temperature and the temperature at which the final shape is achieved is called the finish temperature. In addition, the properties of the alloy at selected temperatures may be varied by the addition of other metals such as copper and niobium. Properties such as elasticity or superelasticity and toughness may be varied and a wide choice of alloys is available. To achieve embodiments of the present invention SMAs with a transformation temperature of approximately 25 to 36° C. preferably 30 to 35° C. would generally be preferred.

For some arrangements a bimetallic strip or similar mechanism constructed of two or more materials with differing coefficients of thermal expansion may provide a cheaper and simpler heat induced shape change suitable for automatically operating a latch at or near body temperature but because of rapid action and precise temperature control an SMA will generally be preferred. A possible disadvantage of an SMA is that shape change could occur irreversibly during storage at high ambient temperature. This potential disadvantage may however be alleviated by providing an elastic return component which returns the SMA to the lower temperature or start condition when a lower ambient temperature such as would prevail in a clinic is restored.

In FIGS. 3 and 4 of the accompanying drawings, there is shown a needle apparatus 40 in accordance with the present invention.

In this second embodiment of the present invention, a housing 12 has a sleeve 18 mounted in the closed end 16 thereof. Further, a metal needle 20 extends into the housing 12 and engages with an aperture in a guide means 28 in the housing 12. In addition a coil spring 26 is mounted about the needle 20 between the end 16 and the guide means 28 and is engaged with a collar 24 which engages securely with the needle 20.

A latch member 42 is mounted on a base member 19. The latch member 42 is formed of an SMA and in the position shown in FIG. 3, engages with an inner end 21 of the needle 20 to prevent the needle 20 from retracting into the housing 12 under urging from the spring 26. However, when the latch member 42 is, in use, heated near to body temperature by heat transfer from the needle 20, it tends to straighten to the position shown in FIG. 4 in which it is disposed away from the end 23 of the needle 20. Thus, the spring 26 acting on the collar 24 causes the needle 20 to be retracted automatically partially into the housing 12 such that the point 22 is disposed within the sleeve 18 by a few millimetres as shown in FIG. 4 and the point 22 is therefore shielded by the sleeve 18. In this condition the apparatus 40 is safe as the sharp point 22 is prevented from piercing tissue by the sleeve 18.

In an alternative preferred arrangement of the second embodiment the movement of the needle 20 may be effected by the shape change of the SMA component, so obviating the requirement for the spring 26. In this alternative the latch member 42 may be located forward of the guide means 28. The latch member may be firmly fixed at one end to the needle 20 and at the other to the housing 12 in such a way that change in shape on warming acts to move the needle 20 into a second position such that the sharp point 22 is within the sleeve 18. Various intermediate arrangements may be applied with the aim of varying the delay in movement of the needle point 22 to a second position and improving the utility of the needle apparatus 40.

In FIGS. 5 and 6 of the accompanying drawings, there is shown a needle apparatus 50. In this third embodiment of the present invention there is shown a metal needle 20 restrained by a tightly fitting collar 52 acting on a stop 28. The collar 52 is mounted about the needle 20. Further, the needle 20 extends through the stop 28 which is connected to a conduit 54. The stop 28 is engaged with an interior wall of a housing 12. Further, another collar 24 is mounted about and tightly engaged with the needle 20 adjacent an end 16 of the housing 12. A coil spring 26 is disposed about the needle 20 between the end 16 and the stop 24. The collar 52 is formed of SMA whereas the collar 24 is not. Heating of the collar 52 by body heat transferred from the needle 20 causes the collar 52 to enlarge and the grip of the collar 52 in the needle 20 to be released. This enables the spring 26 to act on the collar 24 and cause automatic movement of the needle 20 into the body 12.

In FIG. 6 it can be seen that the heating of the collar 52 has allowed the sharp point 22 to move to a position a few millimeters inside a sleeve 18, so shielding the sharp point 22 and preventing the sharp point 22 from piercing tissue.

In FIGS. 7 and 8 of the accompanying drawings there is shown a fourth embodiment of the present invention. A needle apparatus 60 of FIG. 7 shows a metal needle 20 held in a first position by a coiled component 62 and ready to pierce skin and enter tissue. The coil component 62 is formed of SMA. When the component 62 is heated by body heat transferred from the needle 20 the coil thereof tends to contract automatically to the condition shown in FIG. 8. FIG. 8 shows the position reached when the change in shape of to the coil component 62 is brought about by warming by means of body heat, the needle 20 having moved to a second position in which the sharp point 22 is a few millimeters inside a sleeve 18. This shields the sharp point 22 and prevents the sharp point 22 from piercing tissue.

In FIGS. 9 and 10 of the accompanying drawings there is shown a fifth embodiment of the present invention. In this embodiment a needle apparatus 70 has the whole of a metal needle 20 or alternatively a portion 72 of the needle 20 constructed of SMA. In the cool condition shown in FIG. 9 the needle 20 is at maximum length in a first position ready to pierce tissue. The needle 20 extends between a flange member 71 engaged with an internal wall of a housing 12. The needle 20 is firmly engaged by the flange member 71 which is also connected to a conduit 54. FIG. 10 shows the position after warming by body heat and it will be seen that the overall length of the needle 20 is shortened by the SMA adopting a sinuous shape between the flange 71 and an end 16 of the housing 12. Thus, an outer end of the needle 20 moves automatically to a second position in which the sharp point 22 is a few millimetres inside a sleeve 18. This shields the sharp point 22 and the sharp point 22 is prevented from piercing tissue by the sleeve 18. As in other embodiments the housing 12 may incorporate a standard Luer fitting form or any other shape facilitating connection to an external fluid chamber or medication delivery line. In an alternative embodiment it is envisaged that a needle 20 formed partially or wholly of SMA could be substantially straight initially and could contract upon warming whilst remaining substantially straight, so that the sharp point 22 is shielded by the sleeve 18.

In FIGS. 11 and 12 of the accompanying drawings there is shown a sixth embodiment 80 of the present invention in which spontaneous movement of a metal needle 20 from a first position to a second position may be prevented by a stop 81. When it is desired to allow the needle 20 to move automatically from a first position to a second position as a result of warming of an SMA component 82 by body heat the stop 81 is removed by an operator as shown in FIG. 12. In this embodiment with the stop 81 removed and a tightly fitting SMA ferrule 82 mounted about the needle 20 the SMA component 82 is expanded as a result of warming by body heat transferred from the needle 20. The needle 20 is released automatically so that it may slide axially into a second position in which the sharp point 22 is just inside a sleeve 18 as can be seen in FIG. 12. In this position the sharp point 22 is shielded. A further safeguard against inadvertent movement to a second position as a result of storage at high ambient temperature may be incorporated into this and similar embodiments by addition of an outer layer of relatively elastic material such as steel on the ferrule 82 such that the tight fitting of the ferrule 82 on the needle 20 is restored on return to a cooler storage temperature.

In FIGS. 13, 14, 15 and 16 of the accompanying drawings there is shown a seventh embodiment 90 of the present invention in which a metal needle 20 retracts fully within a housing 91 due to the urging of a spring 26 when an SMA collar 102 mounted about the needle 20 expands during warming by body heat transferred from the needle 20 sufficiently to allow the needle 20 to slide automatically within the collar 102. The final (third) position reached allows the housing 91 to be detached as shown in FIG. 15 leaving a catheter 93 with Luer fitting shown as component 110 in FIG. 16 within the tissue where it may be used for the exchange of body fluid or the introduction of drugs. The needle 20 in the housing 91 as shown in FIG. 15 has the sharp point 22 thereof shielded. There is also shown a flash back chamber 92 formed of transparent material and mounted on an inner end of the needle 20.

In FIGS. 17 and 18 of the accompanying drawings there is shown an eighth embodiment 180 of the present invention in which the needle apparatus is arranged for collecting venous blood into a vacuum sampling tube 182 in a housing 184. In FIG. 17 a metal needle 20 is restrained in a first position by an SMA ferrule 181 which in the unchanged cool condition forms a tight fit on the needle 20. In FIG. 18, the ferrule 181 has Enlarged as a result of warming by body heat transferred from the needle 20 and hence does not grip the needle 20, which then moves automatically to a second position due to the urging of a spring 26. This movement of the needle 20 also brings a second sharpened end 168 of the needle 20 into close proximity to a cap 224. Thus, pressure applied in introducing a vacuum sampling tube 182 having a bung 186 at an inner end into the housing 184 causes the point 168 to first pierce the cap 224 then pierce the bung 186, allowing blood to flow into the vacuum tube 182. On removal of the filled vacuum tube leakage of blood is prevented by self sealing of the cap 224. A chamber 176 in the cap 224 acts as a "flashback" chamber allowing the operator to easily determine when a vein has been entered successfully. When a second vacuum sampling tube is inserted movement of the needle 20 from the second position shown in FIG. 18 back to the first position shown in FIG. 17 is prevented by a one-way latch 30.

Figure 19:
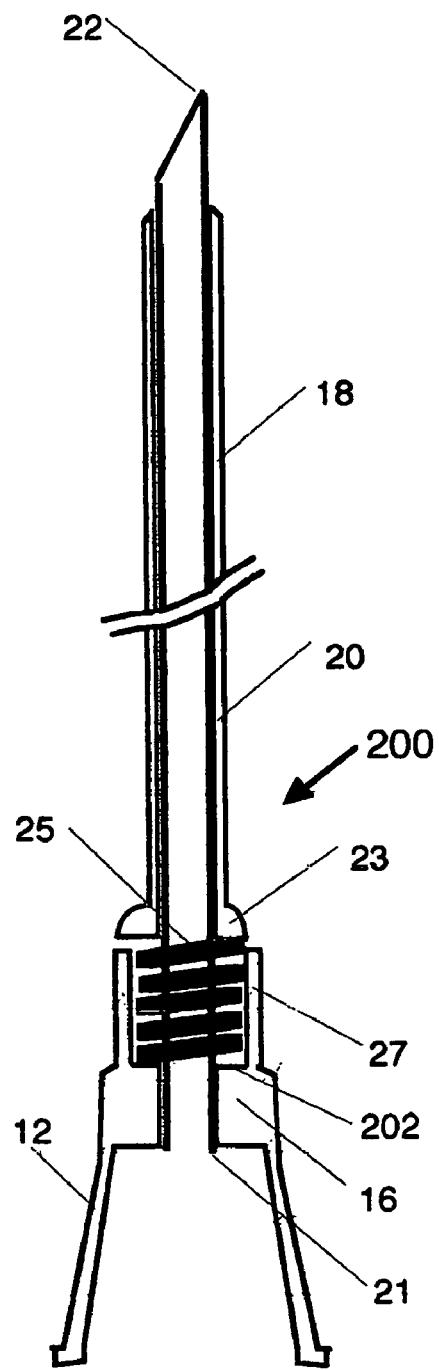
FIG. 19 is a schematic side elevation of a ninth embodiment of a needle apparatus in accordance with the present invention showing the apparatus with a needle point ready for use.
Figure 20:
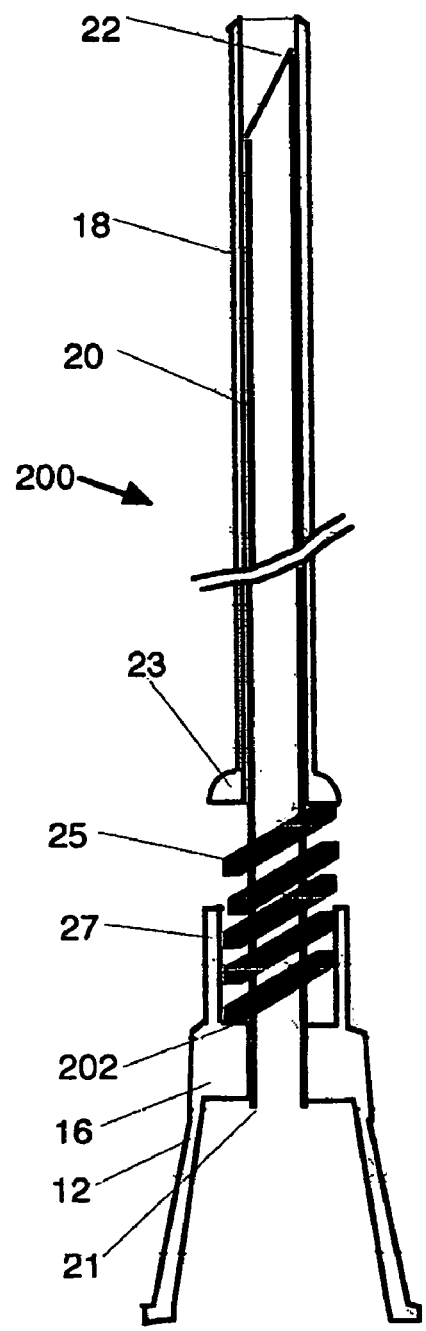
FIG. 20 is a view similar to FIG. 19 showing the apparatus with the needle point retracted.

In FIGS. 19 and 20 of the accompanying drawings there is shown a needle apparatus 200 having a body 12 with a closed end 16. A metal needle 20 is mounted to the end 16 according to a ninth embodiment of the present invention. The needle 20 extends through an aperture in an end wall 202 of the end 16 and is fixedly and sealingly secured to the end 16. A sleeve 18 is mounted about the needle 20 but is not fixed thereto. Preferably, the sleeve 18 forms a fluid tight seal with the needle 20 adjacent an inner end thereof. At this end the sleeve 18 is also provided with an outwardly extending flange 23.

The needle 20 has a sharp point 22 which extends beyond the sleeve 18 in the position show in FIG. 19 at which the apparatus 200 is ready for use.

A coil 25 formed of SMA is mounted about the needle 20 adjacent the end wall 202 and within a cylindrical extension 27 of the wall. The coil 25 is disposed between the end wall 202 and the flange 23 of the sleeve 18.

When the coil 25 is cool it adopts the configuration shown in FIG. 19 in which it is contracted. However, when the coil 25 is heated by body heat transferred from the needle 20 the coil 25 lengthens axially as shown in FIG. 20. This causes the flange 23 to be pushed away from the end 16. Thus, the sleeve 18 is pushed up over the sharp point 22 causing the latter to be shielded by the sleeve 18. This prevents the sharp point 22 from piercing tissue. The coil 25 could be replaced by any equivalent member such as a corrugated generally cylindrical member in which the corrugations straighten out upon heating.

Figure 21:
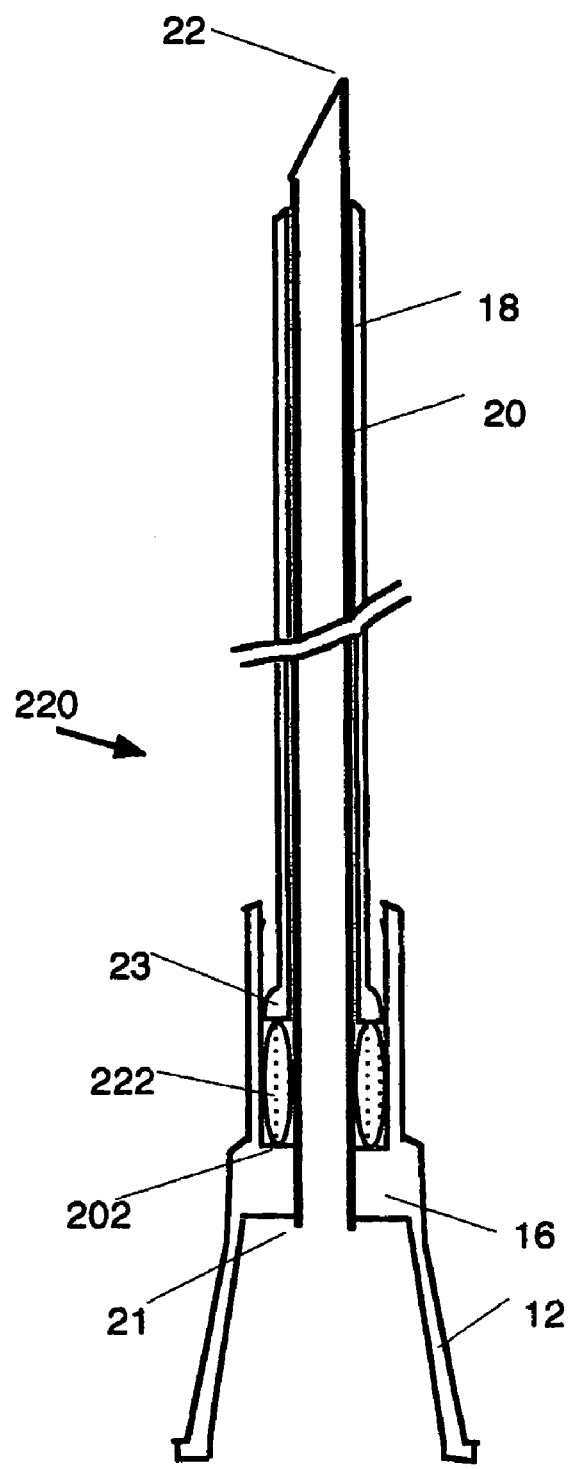
FIG. 21 is a schematic side elevation of a tenth embodiment of a needle apparatus in accordance with the present invention.

In FIG. 21 of the accompanying drawings there is shown a needle apparatus 220 according to a tenth embodiment of the present invention. This embodiment is similar to that of FIGS. 19 and 20 and like reference numerals denote like parts. However, the SMA coil is replaced by an annular container 222 formed of an elastomeric material and filled with a liquid which boils as it is warmed by body heat transferred from the needle 20. The container 222 is maintained in place by enclosure within a cylindrical wall 27 and by an end wall 202. The container 222 expands as it is warmed. The direction of expansion in use is mainly axial causing the expanding container 222 to act on a flange 23 to push a sleeve 18 axially over the sharp point 22 and to, therefore, shield the sharp point 22.

The container 222 could be replaced by any equivalent member such as a coiled tube containing a low boiling point liquid.

Figure 22:
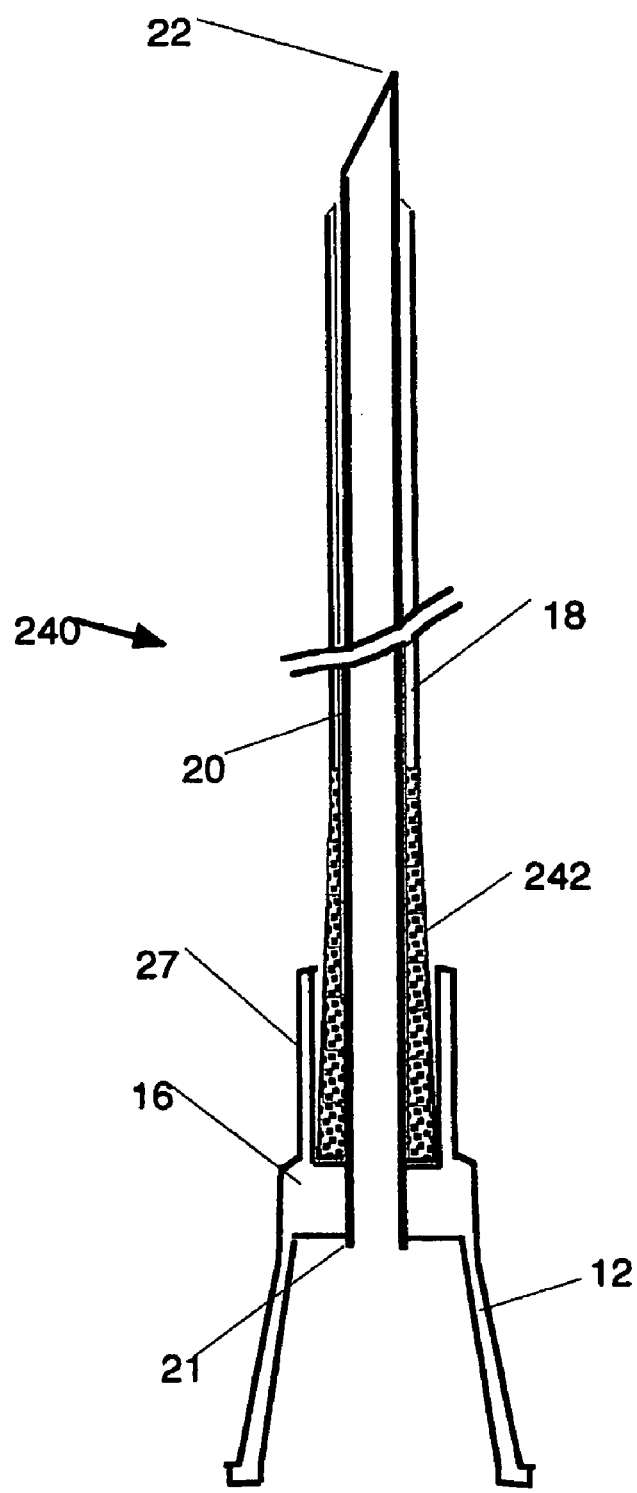
FIG. 22 is a schematic side elevation of an eleventh embodiment of a needle apparatus in accordance with the present invention.

In FIG. 22 of the accompanying drawings there is shown a needle apparatus 240 according to an eleventh embodiment of the present invention. This embodiment is similar to that of FIG. 21 and like reference numerals denote like parts. However, in this case a heat actuator 242 is incorporated into a sleeve 18 adjacent an end 16 of a housing 12. The actuator 242 could be in the form of an SMA coil or multiple globules of low boiling point liquid. In use, body heat transferred from a metal needle 20 causes the sleeve 18 to lengthen axially.

The portion of the sleeve 18 containing the actuator 242 may be formed of elastomer with a softening temperature close to living body temperature whereas the remainder of the catheter may be formed of a plastics material with a higher compression strength and a higher softening temperature.

In use, the pointed needle 20 is pushed against a tissue such as skin or a blood vessel so piercing the tissue and carrying the sleeve 18 partly into the tissue. When in the tissue the needle 20 and the sleeve 18 are heated to near body temperature and heat is conducted to the heat sensitive actuator 242, so causing it to elongate and move the sleeve 18 axially so as to shield the sharp point 22 and so prevent it from inadvertently damaging internal tissues or causing accidental injury when it is withdrawn from the body after use. The transfer of body fluid through the open end of the sleeve 18, the open end of the needle 20, and through the needle 20 will accelerate the transfer of heat to the heat sensitive actuator 242.

If it is desired to inject fluid medication into the tissue that injection fluid is caused to flow in the opposite direction into the needle 20, so tending to cool the heat sensitive actuator 242. In this kind of application, for example where a Luer fitting needle is attached to a syringe, modifications may be made to the design such that the heat sensitive actuator 242 is nearer the injection site and the transformation temperature of the heat sensitive actuator may be lower.

It is desirable that the conditions which cause the heat sensitive actuator 242 to lengthen be precisely regulated and predictable. In hot climates or conditions where cool storage is difficult to arrange or where it is desired to sterilise the needle apparatus 240 by heating it may be necessary to provide a restraint to prevent the heat sensitive actuator 242 from lengthening before change of the apparatus to the second position as desired by the operator. This restraint could take the form of a pin passing transversely through the housing and engaging the distal part of the actuator 242 or alternatively a cap fitted over open ends of the sleeve 18 and the needle 20 and engaging both the sleeve 18 and part of the housing 12, so fixing the sleeve 18. The operator would remove the restraint before or when using the apparatus.

The speed of extension of the actuator 242 can be regulated by choice of transformation temperature, a lower transformation temperature being generally reached more quickly than a higher transformation temperature. An actuator 242 which is in close thermal contact with the needle 20 will also cause a short response time as will good heat insulation around the outside of the actuator 242. A greater sensitivity to tissue temperature and relatively less sensitivity to the temperature of fluid inside the fixed end of the needle 20 may be achieved if desired by the provision of a thermally conducting wire or strip extending from the heat sensitive actuator 242 within or on the wall of the sleeve 18 and extending axially toward a free end of the sleeve 18.

A rapid response time may be preferred for intramuscular or subcutaneous injections whereas a slower response time will usually be preferred where the apparatus is used for entering a vein or other body cavity, for example to collect blood or give fluid medication intravenously.

Figures 23, 24:
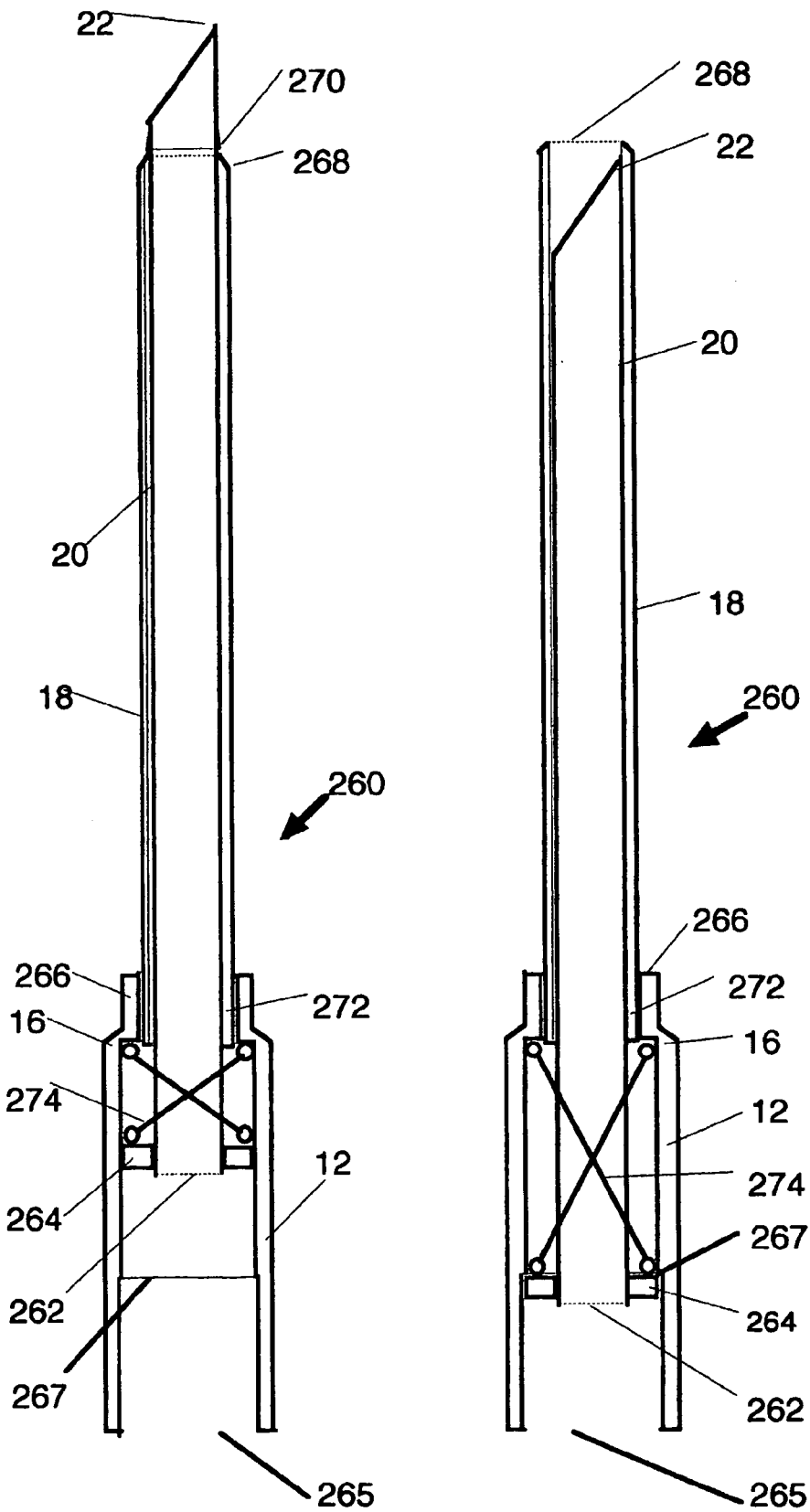
FIG. 23 is a schematic side elevation of a twelfth embodiment of a needle apparatus in accordance with the present invention with a needle point ready for use.
FIG. 24 is a schematic side elevation similar to FIG. 23 in which the needle has retracted so that the needle point is located within a sleeve.

In FIGS. 23 and 24 there is shown a twelfth embodiment of a needle apparatus 260 in accordance with the present invention.

The apparatus includes a metal needle 20 and a sleeve 18 extending around the needle 20. The needle 20 has an inner blunt end 262. The blunt end 262 passes through and is sealingly fixed to a transverse hub 264. The hub 264 is mounted within a substantially cylindrical housing 12 having a smooth internal wall, and forms a flexible seal with the inner surface. The housing 12 has an open end 265 arranged to engage with an external receptacle in known manner.

The housing 12 has a closed end 16 having a central axial hole through which the needle 20 passes. The housing 12 has a forwardly projecting cylindrical member 266 at the end 16. The sleeve 18 is formed of SMA and is closely but slidingly fitted over the needle 20. An outer tip 268 of the sleeve 18 may be slightly inturned to more closely engage the needle 20. The needle 20 may have a slight circumferential groove 270 formed therein to enhance the closeness of the fit with the tip 268 of the sleeve 18 in a first position as shown in FIG. 23.

An inner end 272 of the sleeve 18 is sealingly fixed to the inner surface of the cylindrical member 266. A spring member 274 is disposed between the hub 264 and the end 16 of the housing 12.

In FIG. 24 of a needle apparatus 260 is shown in a second position. As a result of having been warmed above the transformation temperature of the SMA the tip 268 of the sleeve 18 has expanded to a pre-programmed diameter sufficient to free its grip on the needle 20. As a result of urging by the spring 274 the hub 264 slides further into the housing 12 carrying the needle 20 with it so that the needle 20 moves to a second position in relation to the sleeve 18. The inner surface of the housing 12 may if desired have small detentes projecting from the inner surface sufficiently to restrain return of the hub 264 to the first position. Restraint of movement of needle 20 from the first position as shown in FIG. 23 to the second position as shown in FIG. 24 resides almost entirely in the grip of the sleeve tip 268 on the needle 20. In an alternative arrangement this grip may be the result of the tight fit of a part of the length of sleeve 18 on the needle 20, the sleeve 18 acting as a collar. The release of this grip is then the result of an expansion of the diameter of part of the catheter when warmed as programmed into the SMA during construction.

Figure 25:
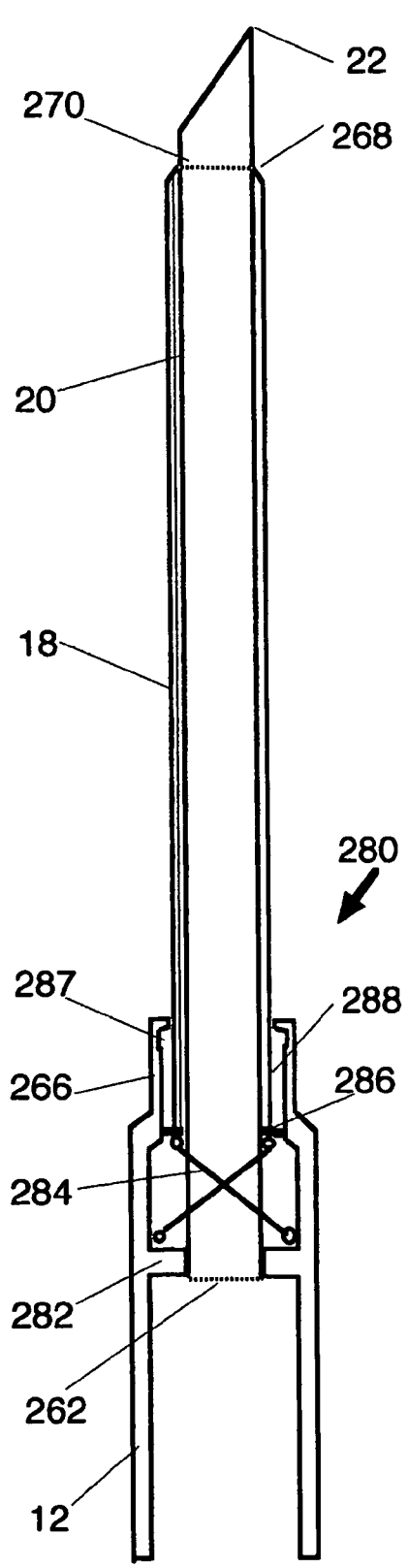
FIG. 25 is a schematic side elevation of a thirteenth embodiment of a needle apparatus in accordance with the present invention with a needle point ready for use.

In FIG. 25 a thirteenth embodiment of a needle apparatus 280 according to the present invention is shown in a first position. Similar parts have similar numbers to those used in FIGS. 23 and 24. In this embodiment the inner end 262 of the needle 20 is firmly and sealingly fixed through a hole in a transverse member 282 formed on an inner wall of a housing 12. A spring 284 is restrained between the transverse member 282 and a base 286 of the sleeve 18. A cavity 288 is disposed between the cylindrical member 266 and the sleeve 18.

Figure 26:
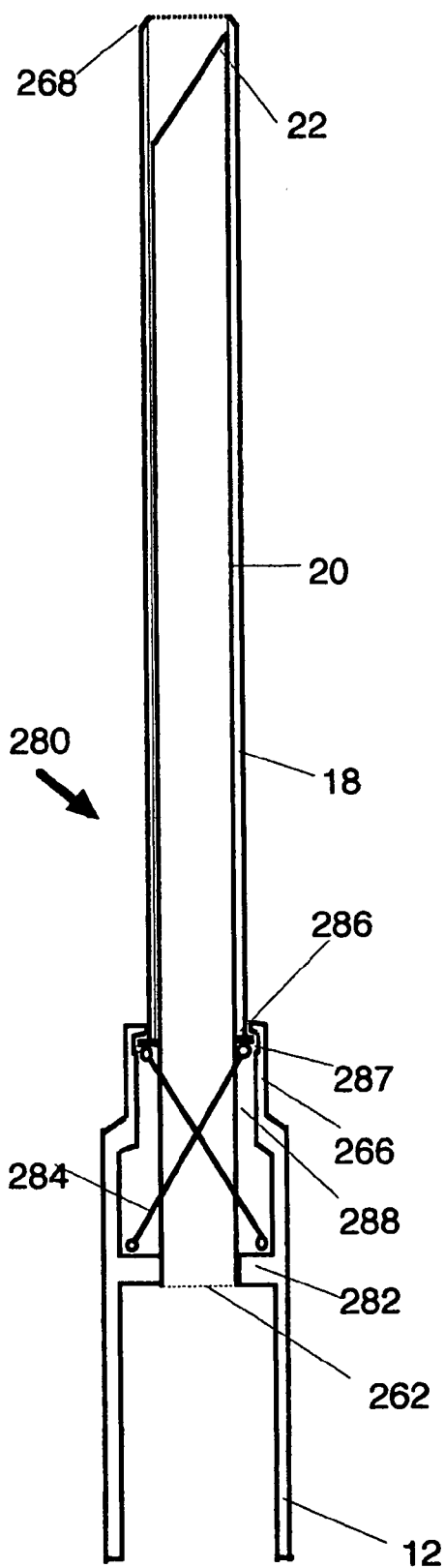
FIG. 26 is a schematic side elevation similar to FIG. 25 in which a sleeve has moved forward axially so that the needle point is located within a catheter.

In FIG. 26 the needle apparatus 280 is shown in a second position in which the tip 268 of the sleeve 18 has changed shape as a result of being warmed above its transformation temperature so that the tip 268 has released its grip on the needle 20, allowing the sleeve 18 to be moved axially by the urging of the spring 284. The base 286 of the sleeve 18 may be expanded or be fitted with an elastic end collar so that it is able to engage reliably the spring 284. Such an expansion or collar may preferably engage a ridge partly closing the cavity 288 to prevent excessive axial movement of the sleeve 18. Fixing an end of the spring 284 to the base 286 of the sleeve 18 can readily provide further restriction of movement. If desired a small inner recess may be formed on an inner wall of the cavity 288 to act as a detente 287 by engaging the base 286 or a collar formed on the base 286 of the sleeve 18. The movement of the sleeve 18 in relation to the needle 20 from the first position as shown in FIG. 25 to the second position as shown in FIG. 26 is chiefly constrained by the shape and dimensions of the tip 268 of the catheter 18. The detente 287 engages with the base 286 to prevent further relative movement of the sleeve 18 and the needle 20 from the position shown in FIG. 26.

In a further alternative embodiment the movement from the first position to the second position of the relative positions of the needle 20 and the sleeve 18 may be restrained by a handle means such as a latch or removable pin so that the operator may choose when this action can occur.

In each embodiment of the automatic needle apparatus of the present invention it is desirable that the movement from a first to a second position should be restrained during storage. A suitable constraint would be a substantially tubular cap the open end of which formed an interference fit with a ridge on the outer surface of the housing and the inner surface of the closed end of which was fitted with a short tube aligned axially and having an inside diameter closely fitting onto and restraining the tip of an SMA catheter. Such a tube could be formed of a metal such as stainless steel or of hard plastic and for convenience would have a conical lead-in to allow ease of assembly over the needle point and sleeve tip as the cap is fitted over the automatic needle assembly.

In the embodiments of the present invention, the sleeve 18 may be rigid or flexible or may be a composite device with, for example, a flexible tip and a rigid base.

It will be appreciated that variations and modifications apparent to a skilled addressee are deemed to be within the scope of the present invention.

What is claimed is:

1. A needle apparatus comprising a tubular needle having a sharp point characterised in that there is provided a shielding means and a movement means for moving the needle and the shielding means relative to one another from an operative position in which the sharp point of the needle is exposed to an inoperative position in which the sharp point of the needle is shielded by the shielding means so as to reduce the possibility of tissue being punctured by the needle, the movement means comprising a component which is responsive to body heat such that when the needle is inserted into tissue, in use, the movement means is exposed to body temperature and the resulting change in temperature of the movement means causes the needle and the shielding means to be moved relatively automatically to the inoperative position, wherein
   (i) the movement means is in the form of a member which is mounted about the needle and which prevents the needle and the movement means from moving relatively to render the needle inoperative until the movement means is exposed to body temperature, or
   (ii) the movement means is located within the needle and the needle is mounted about the movement means such that upon the movement means being exposed to the body heat the movement means and the needle move relatively to render the needle inoperative.

2. A needle apparatus according to claim 1, characterised in that the movement means is responsive to increase in temperature from a relatively low temperature to a temperature close to body heat.

3. A needle apparatus according to claim 1, characterised in that the component which is responsive to body heat contains a shape memory alloy (SMA).

4. A needle apparatus according to claim 3, characterised in that the component which is responsive to body heat is in the form of a blunt insert shielding means located within the needle and formed of SMA, which insert extends in length when the needle is inserted into tissue and the insert is heated by exposure to body heat so as to extend beyond the sharp point of the needle to shield the sharp point of the needle.

5. A needle apparatus according to claim 4, characterised in that the insert is in the form of a coil.

6. A needle apparatus according to claim 3, characterised in that a collar containing SMA is mounted about the needle and grips the needle initially to prevent movement thereof from the operative position, but when the needle is inserted into tissue the collar is heated by exposure to body heat, the collar thus expands and the grip is released so that the needle is able to move to the inoperative position.

7. A needle apparatus according to claim 6, characterised in that the collar is enclosed in a relatively elastic material which allows expansion of the collar upon heating but upon cooling compresses the collar causing it to contract so as to regrip the needle.

8. A needle apparatus according to claim 3, characterised in that the needle is securely mounted in a housing and the needle is enclosed by a sleeve which is axially movable, a component of variable length comprising SMA is mounted about the needle between the housing and the sleeve, such that when the needle is inserted into tissue the component is exposed to body heat and is heated so causing the component to extend in length and to move the sleeve axially thus causing the sharp point to be shielded by the sleeve.

9. A needle apparatus according to claim 8, characterised in that the component is in the form of a coil.

10. A needle apparatus according to claim 3, characterised in that a sleeve is mounted about the needle, the sleeve contains SMA and the sleeve grips the needle, the needle is axially moveable but the movement is restrained by the grip of the sleeve initially, wherein when the needle is inserted into tissue the sleeve is heated by exposure to body heat and is caused to expand so releasing the grip on the needle such that the needle is moved to the inoperative position of the apparatus in which the sharp point is shielded by the sleeve.

11. A needle apparatus according to claim 3, characterised in that a sleeve is mounted about the needle, the sleeve contains SMA and the sleeve grips the needle, the sleeve is axially moveable but the movement is restrained by the grip of the sleeve on the needle initially, wherein when the needle and sleeve are inserted into tissue the sleeve is heated by exposure to body heat and is caused to expand to release the grip on the needle such that the sleeve is moved to the inoperative position of the apparatus in which the sharp point is shielded by the sleeve.

12. A needle apparatus according to claim 3, characterised in that the SMA has a transformation temperature in the range from 25 to 36° C.

13. A needle apparatus according to claim 12, characterised in that the SMA has a transformation temperature in the range from 30 to 35° C.

14. A needle apparatus according to claim 1, characterised in that the component is in the form of an enclosed member containing an expansive fluid, the needle is securely mounted in a housing and the needle is enclosed by a sleeve which is axially movable relative to the needle, the component is mounted about the needle between the housing and the sleeve such that when the needle is inserted into tissue the component is heated by exposure to body heat and extends in length so as to move the sleeve axially to cause the sharp point of the needle to be shielded by the sleeve.

15. A needle apparatus according to claim 1, characterised in that there is provided a latch means to prevent inadvertent relative movement of the needle and the shielding means to the inoperative position prior to use.

16. A needle apparatus according to claim 1, characterised in that the apparatus comprises a two part housing and the needle when in the inoperative position is disposed entirely in a detachable portion of the housing which may be removed from the remaining part.

* * * * *